(12) United States Patent
Fedenia et al.

(10) Patent No.: US 9,907,602 B2
(45) Date of Patent: Mar. 6, 2018

(54) MEDICAL SUCTION AND IRRIGATION DEVICE HANDPIECE

(71) Applicant: ALLEGIANCE CORPORATION, Waukegan, IL (US)

(72) Inventors: Adam S Fedenia, Libertyville, IL (US); Peter L Visconti, Gurnee, IL (US); Michael J. Milella, Jr., Schaumburg, IL (US)

(73) Assignee: ALLEGIANCE CORPORATION, Waukegan, IL (US)

( * ) Notice: Subject to any disclaimer, the term of this patent is extended or adjusted under 35 U.S.C. 154(b) by 0 days.

(21) Appl. No.: 14/997,844

(22) Filed: Jan. 18, 2016

(65) Prior Publication Data
US 2016/0128760 A1 May 12, 2016

Related U.S. Application Data

(62) Division of application No. 11/526,872, filed on Sep. 26, 2006, now Pat. No. 9,259,519.
(Continued)

(51) Int. Cl.
*A61B 17/00* (2006.01)
*A61B 18/12* (2006.01)
(Continued)

(52) U.S. Cl.
CPC ........... *A61B 18/12* (2013.01); *A61M 1/0023* (2013.01); *A61M 1/0035* (2014.02);
(Continued)

(58) Field of Classification Search
CPC ...... A61B 17/2909; A61B 2017/00424; A61B 2217/007; A61B 2217/005; A61M 1/0064;
(Continued)

(56) References Cited

U.S. PATENT DOCUMENTS

| | | | |
|---|---|---|---|
| 3,603,347 A | | 9/1971 | Paolini |
| 4,149,315 A | * | 4/1979 | Page, Jr. ............ A61C 17/0217 |
| | | | 222/571 |

(Continued)

FOREIGN PATENT DOCUMENTS

| | | |
|---|---|---|
| EP | 0807412 A1 | 11/1997 |
| WO | 0228303 A1 | 4/2002 |

OTHER PUBLICATIONS

International Search Report for Application No. PCT/US2006/037540, dated Jan. 18, 2007, 4 pages.
(Continued)

*Primary Examiner* — Gerald Landry, II
(74) *Attorney, Agent, or Firm* — Jacob R. Lenzke

(57) ABSTRACT

Embodiments of the invention are directed to a medical device with a handpiece that provides enhanced comfort of use, maneuverability, and for a variety of hand-held options to the user. Embodiments of the invention include handpieces that include a grip panel comprised of a friction-enhancing material to facilitate gripping of the handpiece by an operator. In addition, embodiments of the invention include handpieces having a generally symmetrical configuration in order to facilitate grasping by an operator's left or right hand.

5 Claims, 14 Drawing Sheets

Related U.S. Application Data

(60) Provisional application No. 60/720,933, filed on Sep. 27, 2005.

(51) Int. Cl.

| | | |
|---|---|---|
| *A61M 1/00* | (2006.01) | |
| *A61M 25/01* | (2006.01) | |
| *A61B 17/221* | (2006.01) | |
| *A61B 17/29* | (2006.01) | |
| *A61B 17/3205* | (2006.01) | |
| *A61B 18/00* | (2006.01) | |

(52) U.S. Cl.
CPC ........ *A61M 1/0039* (2013.01); *A61M 1/0041* (2013.01); *A61M 1/0064* (2013.01); *A61M 25/0136* (2013.01); *A61B 17/221* (2013.01); *A61B 17/2909* (2013.01); *A61B 17/32056* (2013.01); *A61B 2017/00017* (2013.01); *A61B 2017/0046* (2013.01); *A61B 2017/00389* (2013.01); *A61B 2017/00424* (2013.01); *A61B 2017/00464* (2013.01); *A61B 2018/00595* (2013.01); *A61B 2217/005* (2013.01); *A61B 2217/007* (2013.01); *A61M 2205/6036* (2013.01); *A61M 2205/6081* (2013.01)

(58) Field of Classification Search
CPC .............. A61M 1/0039; A61M 1/0023; A61M 1/0041; A61M 1/0031; A61M 25/0136
USPC ....... 601/161; 604/30, 35, 118, 119
See application file for complete search history.

(56) References Cited

U.S. PATENT DOCUMENTS

| | | | |
|---|---|---|---|
| 4,526,573 A | 7/1985 | Lester et al. | |
| 4,931,047 A | 6/1990 | Broadwin et al. | |
| 4,941,872 A | 7/1990 | Felix et al. | |
| 4,957,483 A * | 9/1990 | Gonser | A61C 17/0202 251/149.7 |
| 5,019,054 A * | 5/1991 | Clement | A61B 18/1482 251/209 |
| 5,120,305 A | 6/1992 | Boehringer et al. | |
| 5,147,292 A * | 9/1992 | Kullas | A61M 1/0064 601/161 |
| 5,230,704 A * | 7/1993 | Moberg | A61M 1/0064 604/250 |
| 5,269,750 A * | 12/1993 | Grulke | A61M 1/0064 362/804 |
| 5,306,237 A * | 4/1994 | Clement | A61B 10/04 604/30 |
| 5,322,503 A * | 6/1994 | Desai | A61B 17/00234 604/21 |
| 5,470,305 A | 11/1995 | Arnett et al. | |
| 5,496,314 A | 3/1996 | Eggers | |
| 5,522,796 A | 6/1996 | Dorsey, III | |
| 5,562,640 A * | 10/1996 | McCabe | A61B 17/0218 604/30 |
| 5,607,391 A * | 3/1997 | Klinger | A61B 17/0218 604/33 |
| 5,609,573 A * | 3/1997 | Sandock | A61B 18/1482 604/22 |
| 5,718,580 A | 2/1998 | McFerrin | |
| 5,722,949 A | 3/1998 | Sanese | |
| 5,782,834 A | 7/1998 | Lucey et al. | |
| 5,807,313 A | 9/1998 | Delk et al. | |
| 5,827,202 A | 10/1998 | Miraki et al. | |
| 5,902,264 A * | 5/1999 | Toso | A61B 18/1482 600/130 |
| 5,976,121 A * | 11/1999 | Matern | A61B 17/2909 606/1 |
| 6,068,647 A | 5/2000 | Witt et al. | |
| 6,129,740 A * | 10/2000 | Michelson | A61B 17/2909 606/174 |
| 6,206,870 B1 * | 3/2001 | Kanner | A61B 17/2909 604/523 |
| 6,213,970 B1 | 4/2001 | Nelson et al. | |
| 6,217,587 B1 * | 4/2001 | Tsuruta | A61B 17/221 600/104 |
| 6,623,445 B1 * | 9/2003 | Nelson | A61M 1/0043 604/249 |
| 6,652,488 B1 * | 11/2003 | Cover | A61M 1/0064 604/118 |
| 6,746,419 B1 | 6/2004 | Arnett et al. | |
| 6,988,295 B2 * | 1/2006 | Tillim | A61B 17/2909 16/110.1 |
| 8,002,732 B2 | 8/2011 | Fedenia et al. | |
| 2001/0011162 A1 * | 8/2001 | Epstein | A61B 17/00491 604/30 |
| 2001/0037050 A1 * | 11/2001 | Lemperle | A61B 1/00105 600/135 |
| 2002/0077590 A1 * | 6/2002 | Ponzi | A61B 18/1492 604/95.01 |
| 2002/0082475 A1 * | 6/2002 | Stahl | A61B 1/00147 600/114 |
| 2003/0074766 A1 * | 4/2003 | Tillim | A61B 17/2909 16/430 |
| 2004/0010233 A1 | 1/2004 | Hjertman et al. | |
| 2004/0015137 A1 * | 1/2004 | Hohlfelder | A61M 5/14546 604/246 |
| 2004/0097831 A1 * | 5/2004 | Bourne | A61B 10/0266 600/564 |
| 2004/0158203 A1 | 8/2004 | Cover et al. | |
| 2005/0075600 A1 * | 4/2005 | Nelson | A61M 1/0043 604/35 |
| 2005/0107782 A1 * | 5/2005 | Reschke | A61B 18/1402 606/42 |
| 2005/0192592 A1 * | 9/2005 | Butler | A61B 17/221 606/114 |
| 2006/0121413 A1 | 6/2006 | Turner | |
| 2006/0190034 A1 * | 8/2006 | Nishizawa | A61B 17/29 606/205 |
| 2007/0167918 A1 * | 7/2007 | Reed | A61F 11/002 604/187 |
| 2008/0033348 A1 * | 2/2008 | Bidoia | A61M 1/0064 604/35 |
| 2008/0125762 A1 * | 5/2008 | Hiller | A61B 17/2909 606/1 |

OTHER PUBLICATIONS

Office Action dated Dec. 10, 2012 for European Application No. EP06804180 filed Sep. 26, 2006.
Office Action dated Jan. 16, 2015 for European Application No. EP06804180 filed Sep. 26, 2006.
Written Opinion for International Application No. PCT/US2006/037540, dated Jan. 18, 2007, 7 pages.

* cited by examiner

MEDICAL SUCTION AND IRRIGATION DEVICE HANDPIECE

CROSS REFERENCE TO RELATED APPLICATIONS

This application is a divisional application of U.S. patent application Ser. No. 11/526,872, filed Sep. 26, 2006, titled MEDICAL SUCTION AND IRRIGATION DEVICE HANDPIECE, now U.S. Pat. No. 9,259,519, which claims the benefit of U.S. Provisional Application No. 60/720,933, filed Sep. 27, 2005, under 35 U.S.C. § 119(e), the entire contents of each of which are incorporated herein by reference.

FIELD OF THE INVENTION

The invention relates generally to medical devices, such as, for example, medical devices that provide suction and irrigation during a medical procedure. More particularly, embodiments of the invention relate to hand-held medical devices having features that enhance the maneuverability and/or the comfort of use by an operator.

BACKGROUND OF THE INVENTION

A wide variety of hand-held medical devices are known in the medical field. Certain devices, such as surgical suction and irrigation devices, are intended for relatively long-term hand-held usage. The ease of use, maneuverability, and comfort of use for such devices to the user, therefore, becomes an important consideration in their design. For example, some medical procedures can be relatively lengthy, requiring prolonged handling of certain standard medical devices. Often an operator may have a need to grasp a device alternatively with both the right or left hand. Similarly, an operator may have a need to grasp a device alternatively in positions where the user's hand is oriented in different configurations relative to the handle.

The construction of such devices, therefore, both in terms of its operation as well as the ergonomics of their handling, can have a substantial effect on the successful performance of a medical procedure and its results. Prolonged handling of uncomfortable medical devices can impact the level of precision an operator employs during a medical procedure. As a result, the design and ergonomics of a medical device can have a significant impact on the underlying safety and effectiveness of a medical procedure. Accordingly, there is a need in the medical field, particularly the surgical field, for hand-held devices (e.g., suction-irrigation devices) having features that provide enhanced comfort of use, maneuverability, provide a variety of hand-held options to the user, and which still contain the desired performance and operational structures.

SUMMARY OF THE INVENTION

Accordingly, the present invention is directed to improved hand-held medical devices, and related methods of use that obviate one or more of the limitations and disadvantages of the prior art medical devices. One embodiment of the invention is directed to a handpiece for a medical device, comprising an attachment structure along a front end of the handpiece configured for removably coupling to a medical instrument and a housing. The housing comprises a top surface defining at least one hole for receiving at least one button for controlling a function of the medical device, a bottom base, and an extension portion connected to the base and extending downwardly therefrom. The extension portion includes a shoulder connected to the base by a narrowed neck portion and wherein the base, the shoulder, and the narrowed neck portion define a concave shaped surface capable of receiving an operator's finger.

In various embodiments, the handpiece may include one or more of the following additional features: wherein the housing includes a rear protrusion located along a rear portion of the shoulder; wherein the rear protrusion includes wire retention structure extending upwardly from a top surface of the rear protrusion; wherein the wire retention structure comprises prongs configured to releasably engage a wire; wherein an exterior surface of the handpiece has a substantially symmetrical configuration relative to an imaginary plane that bisects the handpiece through the middle of the top surface, such that the handpiece accommodates an operator's grip in the same manner regardless of whether an operator grasps the handpiece in a right hand or a left hand; wherein a front portion of the handpiece includes indentations located above the base on left and right sides of the handpiece; further comprising a medical instrument, and wherein a proximal portion of the medical instrument includes a rotatable element configured to control the angular orientation of the medical instrument, the rotatable element positioned to permit rotation by a finger of an operator's hand positioned proximate an indentation; wherein the rotatable element comprises a rotatable collar including a plurality of fingertip tabs extending radially away from the collar; wherein a portion of an exterior surface of the housing includes a grip panel extending along a left side, a right side, and a back end of the housing, the grip panel being comprised of a material having a greater friction-enhancing property than a material of a portion of the housing adjacent the grip panel; wherein a rear portion of the housing is configured to accommodate suction and irrigation tubing; wherein the at least one button comprises a suction control button and an irrigation control button; wherein the at least one button comprises an electrocautery actuation button; wherein the suction control button, the irrigation control button, and the electrocautery actuation button are located along substantially the same linear path along the top surface of the housing; wherein the suction and irrigation control buttons are located along a first linear path, and wherein the electrocautery actuation button includes two buttons located along a second linear path substantially perpendicular to the first linear path along the top surface of the housing; wherein the width of the housing decreases toward a proximal end of the housing; and wherein the shoulder has an underside surface having a generally concave shaped, curved surface.

Another embodiment of the invention is directed to a handpiece for a medical device, comprising an attachment structure along a front end of the handpiece configured for removably coupling to a medical instrument and a housing. The housing comprises a top surface defining at least one hole for receiving at least one button for controlling a function of the medical device and a grip panel extending along a left side, a right side, and a back end of the housing. The grip panel is comprised of a material having a greater friction-enhancing property than a material of a portion of the housing adjacent the grip panel. An exterior surface of the handpiece exhibits a substantially symmetrical configuration relative to an imaginary plane that bisects the handpiece through the middle of the top surface, such that the handpiece accommodates an operator's grip in the same manner regardless of whether an operator grasps the handpiece in a right hand or a left hand.

In various embodiments, the handpiece may include one or more of the following additional features: a bottom base and an extension portion connected to the base and extending downwardly therefrom, the extension portion including a shoulder connected to the base by a narrowed neck portion and wherein the base, the shoulder, and the narrowed neck portion define a concave shaped surface capable of receiving an operator's finger; wherein the handpiece includes a rear protrusion located along a rear portion of the shoulder; wherein the rear protrusion includes wire retention structure extending upwardly from a top surface of the rear protrusion; wherein the wire retention structure comprises prongs configured to releasably engage a wire; wherein a front portion of the handpiece includes indentations located above the base on left and right sides of the handpiece; further comprising a medical instrument, and wherein a proximal portion of the medical instrument includes a rotatable element configured to control the angular orientation of the medical instrument, the rotatable element positioned to permit rotation by a finger of an operator's hand positioned proximate an indentation; wherein the rotatable element comprises a rotatable collar including a plurality of fingertip tabs extending radially away from the collar; wherein a rear portion of the housing is configured to accommodate suction and irrigation tubing; wherein the at least one button comprises a suction control button and an irrigation control button; wherein the at least one button comprises an electrocautery actuation button; wherein the suction control button, the irrigation control button, and the electrocautery actuation button are located along substantially the same linear path along the top surface of the housing; wherein the suction and irrigation control buttons are located along a first linear path, and wherein the electrocautery actuation button includes two buttons located along a second linear path substantially perpendicular to the first linear path along the top surface of the housing; wherein the width of the housing decreases toward a proximal end of the housing; and wherein the shoulder has an underside surface having a generally concave shaped, curved surface.

Another embodiment of the invention is directed to a method for operating a medical device to perform a medical procedure, comprising providing a medical device comprising a medical instrument connected to a front end of a handpiece, the handpiece including an attachment structure along a front end thereof configured for removably coupling to the medical instrument. The handpiece further comprises a housing having a top surface defining at least one hole for receiving at least one button for controlling a function of the medical device, a bottom base, and an extension portion connected to the base and extending downwardly therefrom, the extension portion including a shoulder connected to the base by a narrowed neck portion. The base, the shoulder, and the narrowed neck portion define a concave shaped surface capable of receiving an operator's finger. The method further comprising grasping the handpiece with one of a left hand or a right hand such that the operator's thumb rests over the control button, and an operator's finger rests on the concave shaped surface, and wherein the handpiece is capable of being grasped by the left hand or the right hand in the same manner. The method further comprises positioning the medical instrument and actuating the control button to perform a medical procedure.

In various embodiments, the method may include one or more of the following additional features: wherein actuating the control button comprises one of supplying suction or irrigation to the medical instrument; wherein actuating the control button comprises providing electric current to the medical instrument; and wherein a proximal portion of the medical instrument includes a rotatable element configured to control the angular orientation of the medical instrument, the method further comprising rotating the rotatable element with a finger of the same hand used to grasp the handpiece in order to change the angular orientation of the medical instrument relative to the handpiece.

Another embodiment of the invention is directed to a method for operating a medical device to perform a medical procedure, comprising providing a medical device comprising a medical instrument connected to a front end of a handpiece and a handpiece including an attachment structure along a front end thereof configured for removably coupling to the medical instrument. The handpiece further comprises a housing including a top surface defining at least one hole for receiving at least one button for controlling a function of the medical device, a grip panel extending along a left side, a right side, and a back end of the housing, the grip panel being comprised of a material having a greater friction-enhancing property than a material of a portion of the housing adjacent the grip panel. An exterior surface of the handpiece exhibits a substantially symmetrical configuration relative to an imaginary plane that bisects the handpiece through the middle of the top surface. The method further comprises grasping the handpiece with one of a left hand or a right hand such that the operator's thumb rests over the control button, and an operator's finger rests on the concave shaped surface, the handpiece capable of being grasped by the left hand or the right hand in the same manner. The method further comprises positioning the medical instrument and actuating the control button to perform a medical procedure.

In various embodiments, the method may include one or more of the following additional features: wherein the handpiece includes a base and an extension portion connected to the base and including a shoulder having an underside surface having a generally concave shaped, curved surface, and wherein grasping the handpiece comprises receiving the concave shaped, curved surface of the shoulder within an operator's palm within a valley between an operator's thumb and index finger; wherein actuating the control button comprises one of supplying suction or irrigation to the medical instrument; wherein actuating the control button comprises providing electric current to the medical instrument; and wherein a proximal portion of the medical instrument includes a rotatable element configured to control the angular orientation of the medical instrument, the method further comprising rotating the rotatable element with a finger of the same hand used to grasp the handpiece in order to change the angular orientation of the medical instrument relative to the handpiece.

Another embodiment of the invention is a handpiece for a medical device including a right half and a left half configured to be coupled together to form a housing. An exterior surface of the right half is a substantially mirror image of an exterior surface of the left half, the right half and the left half when coupled together defining a first hole in the top surface of the housing for receiving a button of the handpiece, a second hole in a back end of the housing for receiving a tube, and a third hole in a front end of the housing for receiving a medical instrument.

In various embodiments, the handpiece may include one or more of the following additional features: a bottom base and an extension portion connected to the base and extending downwardly therefrom, the extension portion including a shoulder connected to the base by a narrowed neck portion and wherein the base, the shoulder, and the narrowed neck portion define a concave shaped surface capable of receiving an operator's finger; the housing further comprising a grip panel extending along a left side, a right side, and the back end of the housing, the grip panel being comprised of a material having a greater a friction-enhancing property than a material of a portion of the housing adjacent the grip panel; and wherein the handpiece accommodates an operator's grip in the same manner regardless of whether an operator grasps the handpiece in a right hand or a left hand.

Another embodiment of the invention is directed to a method for operating a medical device to perform a medical procedure, comprising providing a medical device comprising a medical instrument. The handpiece includes a right half and a left half configured to be coupled together to form a housing, an exterior surface of the right half being a substantially mirror image of an exterior surface of the left half, the right half and the left half when coupled together defining a first hole in a top surface of the housing for receiving a button of the handpiece, a second hole in a back end of the housing for receiving a tube, and a third hole in a front end of the housing for receiving the medical instrument. The method further comprises grasping the handpiece with one of a left hand or a right hand, the handpiece capable of being grasped by the left hand or the right hand in the same manner, positioning the medical instrument, and actuating the control button to perform a medical procedure.

In various embodiments, the method may include one or more of the following additional features: wherein the handpiece includes a base and an extension portion connected to the base and including a shoulder having an underside surface having a generally concave shaped, curved surface, and wherein grasping the handpiece comprises receiving the concave shaped, curved surface of the shoulder within an operator's palm within a valley between an operator's thumb and index finger; wherein actuating the control button comprises one of supplying suction or irrigation to the medical instrument; and wherein actuating the control button comprises providing electric current to the medical instrument.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION

Reference will now be made in detail to the present exemplary embodiments of the invention illustrated in the accompanying drawings. Wherever possible, the same reference numbers will be used throughout the drawings to refer to the same or like parts. For purposes of this disclosure, "distal" refers to the end further from the device operator during use and "proximal" refers to the end closer to the device operator during use.

Figure 1:
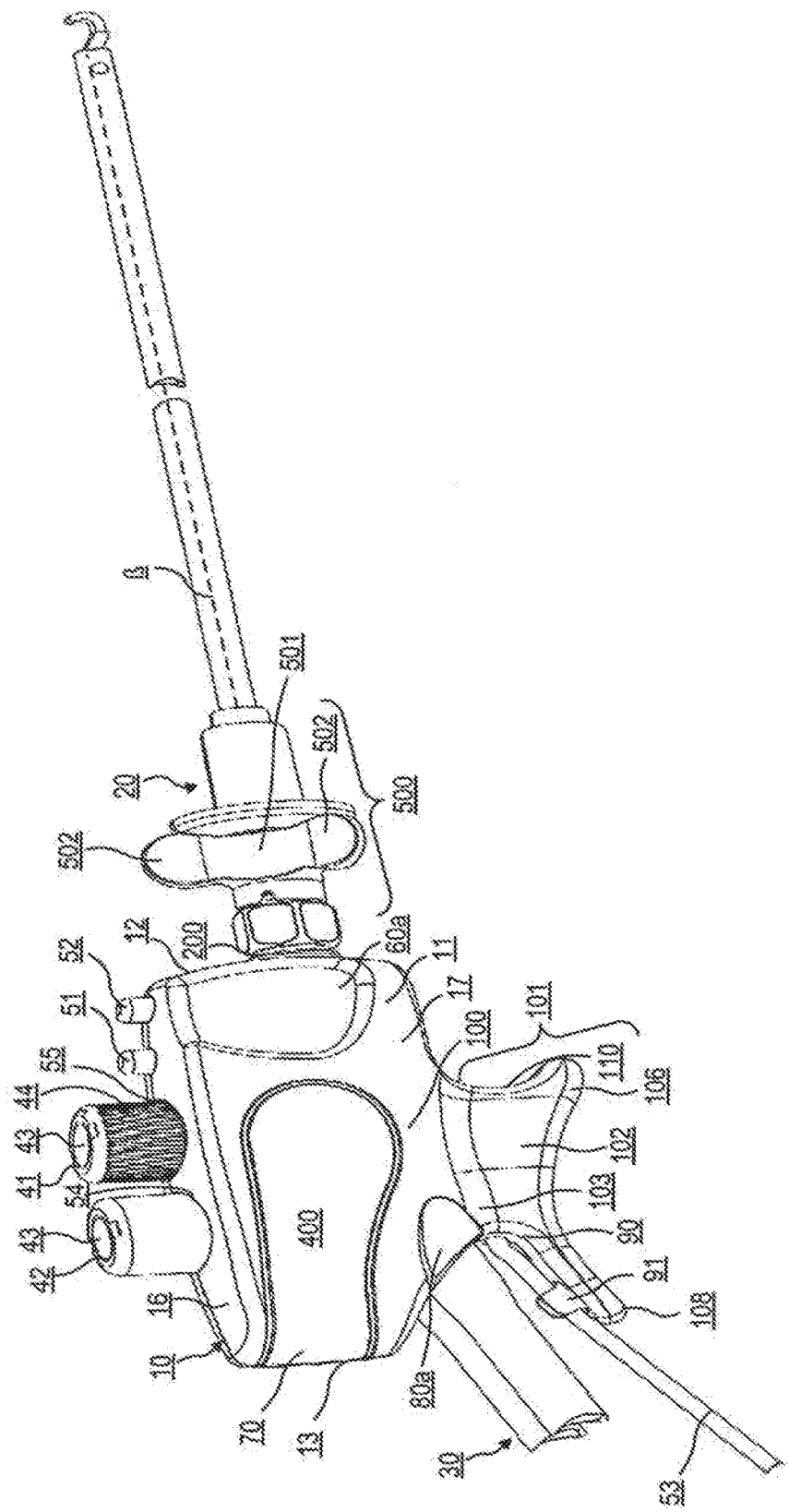
FIG. 1 is an angled side view of a medical device handpiece having an instrument connected at a front end thereof, according to an embodiment of the present disclosure.

Referring to FIG. 1, one embodiment of a medical device, according to the invention, includes a handpiece 10 onto which a medical instrument 20 (shown as a probe), can be removably coupled or uncoupled (see FIG. 2), and into which tubing 30 (e.g., suction and irrigation tubing) can be attached. While medical instrument 20 is depicted as a probe (or alternatively as an electrosurgical probe), instrument 20 may comprise a basket, a grasper, a snare, any other retrieval or grasping mechanism, a tissue cutting instrument, any electrocautery device, a forceps, or any other mechanism for performing an operation in a body that may be suitable for a medical diagnostic or treatment procedure.

In this disclosure, handpiece 10 is primarily described as a handpiece for use in a medical suction and irrigation device. The device 10 may connect a source of irrigation fluid, such as a saline bag (not shown). The irrigation fluid may be supplied to the handpiece through tubing 30 via a pump unit (not shown). The pump unit may include, for example, a motor, impeller, power source, and other conventional parts known in the art. The device 10 may also connect to a source of suction, such as a conventional vacuum source available in a hospital room setting. Suction would be supplied through tubing 30. Device 10 further may connect to a source of electric current via wires 53, for supplying electrocautery to a patient. It is to be understood, however, that some or all of the aspects of the handpiece 10 could be used with other types of medical devices.

Figure 3:
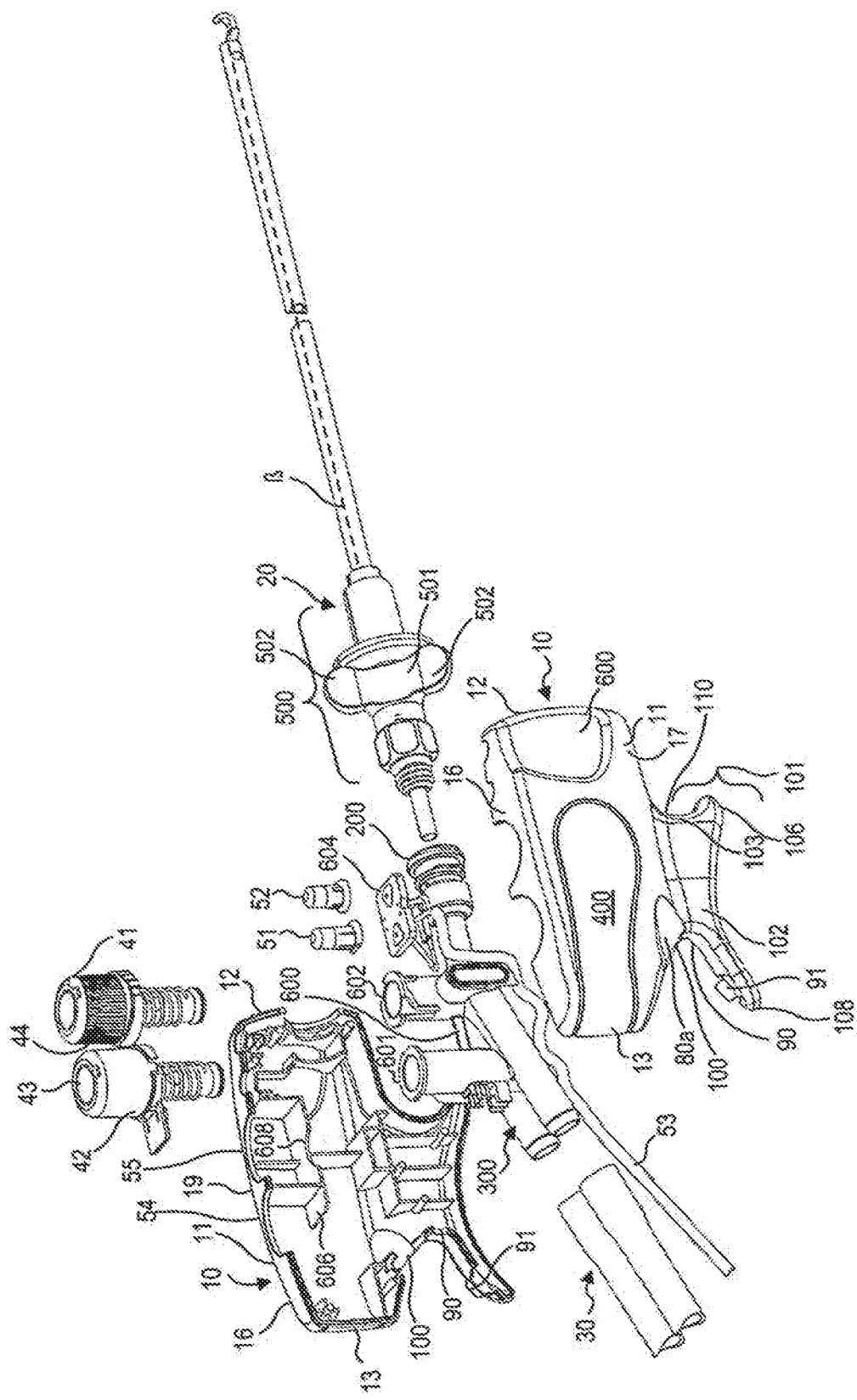
FIG. 3 is a disassembled view of a medical device handpiece and an instrument, according to an embodiment of the present disclosure.
Figure 4:
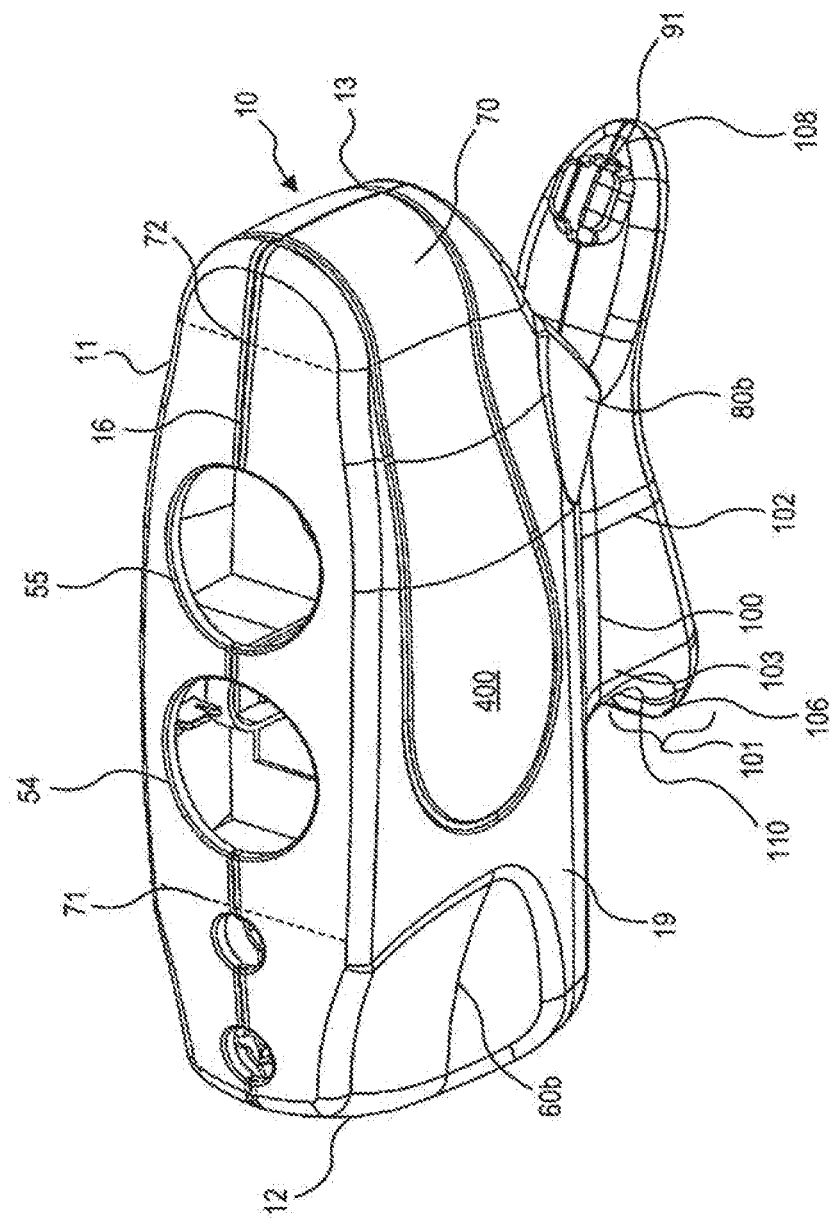
FIG. 4 is an angled side view of a medical device handpiece housing, according to an embodiment of the present disclosure.

The handpiece 10 is defined by a housing 11 that includes a front end 12, a back end 13, a first (right) half 17, and a second (left) half 19 (see FIGS. 3-4). The housing 11 of handpiece 10 further includes a top surface 16 circumscribed by the first and second halves 17, 19 and the front and back ends 12, 13. A lower portion of the handpiece 10 includes a base 100 circumscribed by the first and second halves 17, 19 as well as the front and back ends 12, 13.

As seen in FIG. 1, the front end 12 of the housing 11 extends to an instrument attachment structure 200 within housing 11 for removably coupling a medical instrument 20 thereon. In the illustrated example, the attachment structure comprises an internal threaded element configured for mating with external threads along a proximal portion of medical instrument 20. Such a coupling arrangement is exemplary, and other coupling structure is contemplated for structure 200. Alternative examples of attachment structure 200 include, but are not limited to, adhesives, pin and grooved channel mating structures, friction fit engagement structures, and releasable resilient male/female mating structures.

In the illustrated embodiment, the handpiece 10 of the medical device includes the additional components of a suction control button 41 and an irrigation control button 42. The top surface of control buttons 41 and 42 may each include a concave depression 43 for facilitating reception of an operator's fingertips for actuation thereof. The control buttons 41 and 42 may have certain characteristics to visually distinguish one button from the other. For example, as seen in FIG. 1, suction control button 41 may have a knurled pattern 44 along an exterior side surface, whereas irrigation control button 42 has a smooth exterior side surface. Other distinguishing characteristics are contemplated, such as a difference in color, for example. In addition, the handpiece 10 of medical device may include additional operative mechanisms such as electrical control buttons 51 and 52 for operative coupling to electrical wiring 53, to permit connection to an additional power source (not shown), for example.

In one embodiment, wiring 53 may connect to a source of electric current and buttons 51 and 52 are actuated to selectively supply current to medical instrument 20. The supply of current may be used to assist in cutting and/or cauterizing tissue. The suction and irrigation control buttons 41, 42 (and electric control buttons 51 and 52, when included) may be located within holes 54 and 55 defined by the top surface 16. In the embodiment of handpiece 10 depicted in FIG. 1, the control buttons 41, 42, 51, and 52 are all provided along substantially the same longitudinal path along the top surface 16. In this location, the control buttons will be accessible for actuation by an operator's fingertips, or alternatively by an operator's thumb, depending on the operator's grasping orientation, as will be described in more detail below.

As seen at least FIGS. 1-4, the handpiece 10 contains an inward arcuate indented portion 60a in a region located between the front end 12 and the first (right) half 17 of housing 11. Similarly (as seen in FIG. 4, for example), the handpiece 10 contains an inward arcuate indented portion 60b in a region located between the front end 12 and the second (left) half 19. Along the back portion of the handpiece 10, a contiguous outward arcuate curve 70 may be provided in a region defined by the first and second halves 17, 19 and the back end 13 of the housing 11. As seen in FIGS. 1 and 4, adjacent the back end 13 on both right half 17, and left half 19, the handpiece 10 includes arcuate curved protrusions 80a and 80b. Protrusions 80a and 80b define a hole that accommodates tubing 30 within the housing 11.

As will be described in more detail below, the handpiece 10 may further include a contiguous grip panel 400 located along the first and second half 17, 19 and the back end 13 of the housing 11. Alternatively, a grip panel may only cover certain portions of either side of the housing 11 (e.g. only one side), and not the back end 13. The color of panel 400 may differ from the color of the remainder of housing 11. The grip panel 400 is composed of a friction-enhancing material to facilitate gripping of the handpiece 10 by an operator, thereby affording greater accuracy and precision in the maneuvering and manipulating the medical device. Exemplary materials for the grip panel 400 include, but are not limited to, thermoplastic elastomeric materials (TPEs), rubber materials, and polymers.

As seen in FIG. 1, a lower portion of handpiece 10 includes a base 100 located below the indented portions 60a, 60b and the grip panel 400. The base 100 comprises a lower portion of the handpiece 10 and exhibits an inwardly directed curve on each half 17, 19 such that the thickness of the handpiece 10 decreases in a downward direction as compared to a thickness of the handpiece along the grip panel 400, for example. The base 100 is circumscribed by first and second halves 17, 19 and including the front and back ends 12 and 13.

As seen in FIG. 1, the base 100 of the handpiece housing 11 is connected to, or continues downwardly to form, an extension portion 101. The extension portion 101 includes a shoulder portion 102 connected to the remainder of the housing 11 by an inwardly curved, narrow neck portion 103. As seen in FIG. 1, the shoulder portion 102 extends below the neck portion 103 and comprises a generally oblong shape. The shoulder portion 102 includes a front protrusion 106 and a rear protrusion 108. As will be described in more detail below with regard to FIG. 5, the shoulder portion 102 has an underside surface 104 (see FIG. 5) having a curve along its longitudinal axis α (alpha). As will be described, the shoulder portion 102 and curve 6 afford additional gripping options to the user for the handpiece 10.

The rear protrusion 108 extends from the rear end of the narrowed neck portion 103 and, in one example, includes at least two features for accommodating wiring 53 associated with handpiece 10. For example, as seen in FIG. 1, when electrical features are included in the medical device, preferably the back end of handpiece 10 further comprises structure for accommodating electrical wire or wires. In the illustrated embodiment, the accommodating structure includes both an entrance port 90 leading into the handpiece housing 11, as well as a wire retention structure 91 extending upwardly from the surface of the rear protrusion 108. The wire retention structure 91 may comprise left and right prongs that extend upwardly from the surface of the rear protrusion 108 to releasably engage opposite sides of wire 53 (e.g., by virtue of an interference fit). Whereas tubing will typically be rigid enough to substantially maintain a predetermined configuration in proximity to the handpiece 10, wiring (such as wiring 53) may be more flexible. The wire retention structure 91 provides the benefit of controlling displacement and migration of the wire 53 during operation of the device.

As seen in FIG. 1, the front protrusion 106 extends from the front end of the narrowed neck portion 103. The front protrusion 106 extends distally from the narrowed neck portion by a distance less than the distance rear protrusion 108 itself extends proximally from the narrowed neck portion 103. In one embodiment, the front protrusion 106 extends from the narrowed neck portion 103 so as to form a concave shaped trigger surface 110 along with a front portion of the narrowed neck portion 103 as well as an underside of a front portion of the base 100.

As will be described in more detail below with regard to FIGS. 11A-11B and 12A-12B, the concave surface 110 provides an engagement surface particularly suited for receiving the palm side an operator's finger, or fingers. Accordingly, the concave shaped trigger surface 110 provides a force reaction surface configured to receive a palm side of at least one of an operator's fingers. As a result, during use, an operator can comfortably and stably grasp the handpiece 10 between at least one finger along a front surface of the handpiece 10 and the base of the operator's palm along a rear surface of the handpiece 10. As an alternative arrangement, it is contemplated that a tip of the protrusion 106 be connected to an underside of a front portion of the base 100, thereby forming an aperture for receipt of an operator's fingers.

Figure 2:
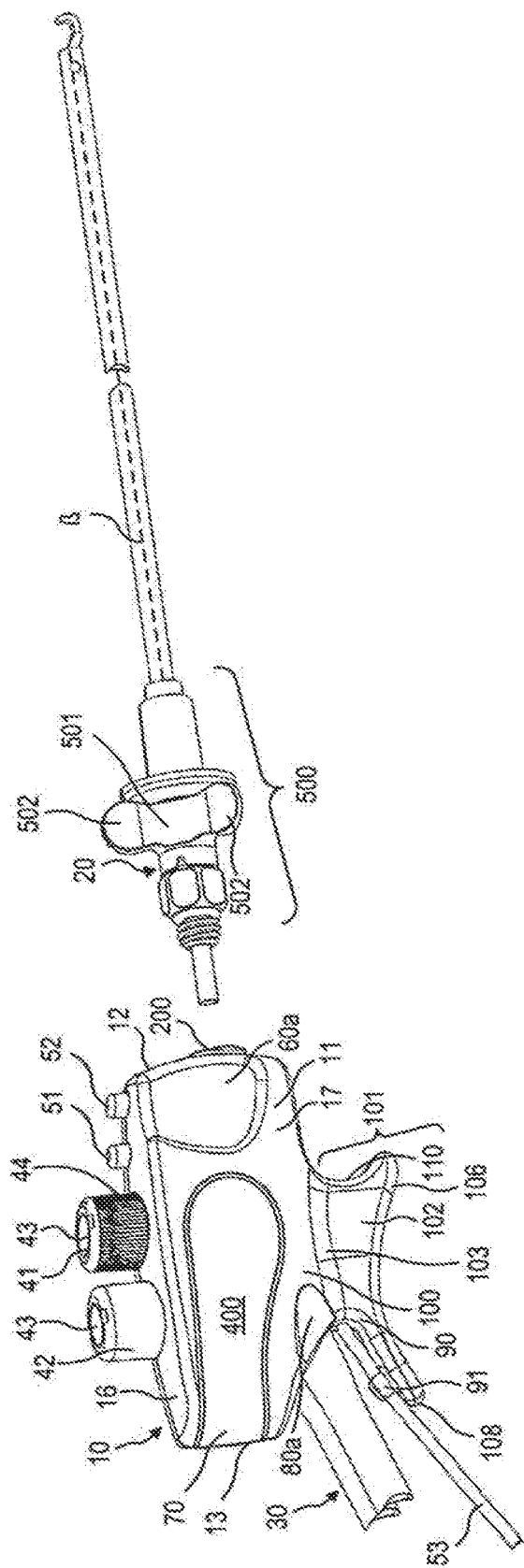
FIG. 2 is an angled side view of a medical device handpiece having an instrument spaced from a front end thereof, according to an embodiment of the present disclosure.

FIG. 2 shows an angled side view of a medical device having an instrument spaced from a front end 12 of the handpiece 10. As noted above, the front end 12 of the handpiece 10 accommodates an instrument attachment structure 200 for removably coupling a medical instrument 20 thereon. As seen in FIGS. 1-3, and with particular reference to FIG. 2, the medical instrument 20 may include a probe hub assembly 500 structured to removably engage the probe attachment structure 200 on the handpiece 10. Upon engagement of the medical instrument 20 to the handpiece 10, manipulation of handpiece 10 in turn results in controlled operation of medical instrument 20. For example, operation of buttons 51, 52 may cause electric current to be supplied to the tip of instrument 20. As further examples, operation of buttons 41, 42 may respectively cause suction to be applied through instrument 20 and a supply of irrigation fluid through instrument 20. When using a probe hub assembly 500 that is structured to permit rotation about the longitudinal axis β (beta) of the medical instrument 20 located on the distal end, the probe hub assembly 500 can comprise a rotatable collar 501 positioned to permit rotation by a finger of the hand wherein the handpiece is held by one hand (as shown in FIGS. 11B and 12B).

FIG. 2 also depicts an embodiment wherein the rotatable collar 501 comprises a plurality of fingertip tabs 502 to further facilitate the rotation of the instrument 20. Finger tabs 502 may comprise relatively flat projections extending radially outward from the base of the rotatable collar 501. In the illustrated embodiment, there are three equally spaced tabs 502. Three tabs is only exemplary, and more or fewer tabs may be incorporated in assembly 500. Finger tabs 502 extend radially from collar 501 in order to be manipulated by an operator's finger to effectuate rotation of the instrument 20.

In one embodiment, the medical instrument 20 comprises an electrocautery probe having an end effector forming a hook 503 configured to manipulate tissue and provide electrocautery to control patient bleeding during surgery, for example. After grasping the handpiece 10, an operator can control the angular orientation of the hook 503 relative to the longitudinal axis β (beta) of the medical instrument 20 with the fingers of the same hand use to grasp handpiece 10. Manipulation of the fingertip tabs 502 via an operator's fingers is further facilitated due to the clearance space provided by virtue of the inward arcuate indented portions 60a and 60b provided along the first and second halves 17, 19 of housing 11. Providing the indented portion 60a and 60b on both halves 17, 19 of the handpiece allows manipulation of the fingertip tabs 502 alternatively with fingers of an operator's left hand or right hand.

Referring to FIG. 3, a disassembled view of a medical device is depicted. More particularly, FIG. 3 depicts an exploded view of the internal and external structure of a medical suction and irrigation device. In FIG. 3, the first (right) half 17 is separated from the second (left) half 19. The first and second halves 17 and 19 may each be formed through a molding process such that they are configured to receive the internal components therebetween. During manufacture and assembly, the first and second halves 17, 19 may enclose the internal device components upon a mating engagement therebetween. For example, the interior of the first half 17 may include male pin mating protrusions configured for receipt within female pin apertures formed on the interior of the second half 19.

As seen in FIG. 3, the internal components of the handpiece 10 may include the internal electric wiring 53, a manifold assembly 600, irrigation and suction valve piston housing chambers 601 and 602 respectively, and an conducting platform 604 for providing a transmission path for an electric circuit from wiring 53 to the control buttons 51 and 52. The manifold assembly 600 includes structure for routing suction and irrigation flow-paths in a predetermined configuration to a distal end of the handpiece where the pathways connect to an appropriate conduit within a distal medical instrument. As illustrated, each housing half may include internal structure, such as preformed protrusions 606 defining separate chambers within the inside of each housing half, for receiving a particular component of the manifold assembly 600 and/or the wiring structure 53. For example, the second half 19 may include a protrusion 606 having a portion defining a semicircle configuration 608 for snugly receiving the exterior portion of the suction piston housing chamber 602. Similarly, the pattern of protrusions may be particularly provided to accommodate the path of wiring 53 within the handpiece housing 11.

As seen in FIGS. 1-3, the configuration of the exterior surface of the handpiece 10 exhibits a substantially symmetrical configuration relative to an imaginary plane that bisects the handpiece 10 through the top surface 16. As such, the handpiece 10 will conform in the same manner regardless of whether an operator grasps the handle in the right hand or the left hand. In addition, in at least one embodiment, the first and second halves 17, 19 of the handpiece housing 11 are configured to be coupled together. In one embodiment, the exterior surface of the right half 17 is substantially a mirror image of the exterior surface of the left half 19, the right half 17 and left half 19 when coupled together define holes for receiving the control buttons 41, 42, the tubing 30, wiring 53, and attachment structure 200.

Exemplary mechanical and electrical internal components of the medical device are described in U.S. application Ser. No. 11/526,871 filed on Sep. 26, 2006, and now issued as U.S. Pat. No. 8,002,732, the entire contents of which is hereby incorporated by reference. Engagement of the first and second halves 17, 19 may be effectuated by virtue of a snap fit arrangement, the use of suitable medical grade adhesive, or any other suitable alternative mechanical engagement. Non limiting examples of materials suitable for forming the handpiece housing 11 include, but are not limited to acrylonitrile-butadiene-styrene (ABS), styrene-acrylonitrile copolymer (SAN), polyvinyl chloride (PVC), polycarbonate (PC), and polystyrene (PS).

FIG. 4 shows an angled side view of the housing of a medical device handpiece. Handpiece housing 11 illustrated in FIG. 4 is identical to the handpiece housing 11 depicted in FIGS. 1-3. In FIG. 4, however, the handpiece is depicted without the control buttons 41, 42, 51, and 52 and various internal and external components. FIG. 4 illustrates a first imaginary line 71 across the width along the top portion 16 of the handpiece housing 11. FIG. 4 also depicts a second imaginary line 72 across the width along a top portion 16 of the handpiece housing. As seen, the first line 71 is located along the top surface 16 adjacent to the front end 12 between the first and second halves 17 and 19 and just proximal of the inward arcuate indentations 60a and 60b. The second line 72 is located adjacent to the back end 13 of the housing 11 and just distal of the outward arcuate curve 70. In the illustrated embodiment, the width of the housing 11 depicted along line 71 is greater than the width of the housing depicted along line 72 (see also FIG. 7). Accordingly, in one embodiment, the width of the handpiece housing 11 decreases toward a proximal end of the handpiece housing 11.

Figure 5:
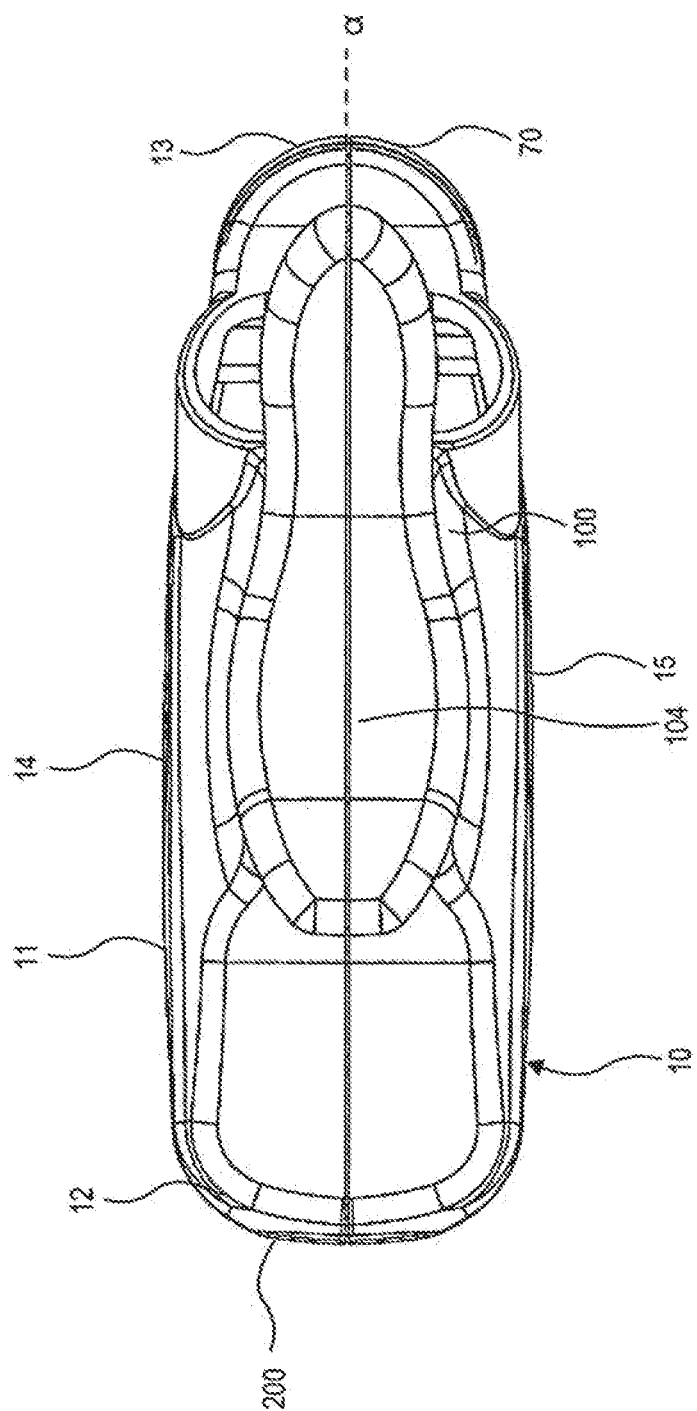
FIG. 5 is a bottom view of a medical device handpiece housing, according to an embodiment of the present disclosure.

FIG. 5 depicts a bottom view of the housing 11 of a medical device handpiece 10 of FIGS. 1-4. As described above, the shoulder portion 102 has an underside surface 104 having a generally concave shaped, curved surface along its longitudinal axis α (alpha). The shoulder portion 102 and concave curved shape of surface 104 afford additional gripping options to the user for the handpiece 10. As will be described in more detail below with regard to FIGS. 11C-11D and 12C-12D, the concave, curved surface 104 provides an engagement surface particularly suited for receipt within an operator's palm within the valley between an operator's thumb and index finger. In such a grasping position, an operator manipulates the control buttons with any of the fingertips while grasping opposite sides of the gripping panel 400 between the thumb and a portion of the same hand where the operator's palm meets the base of the fingers.

Figure 6:
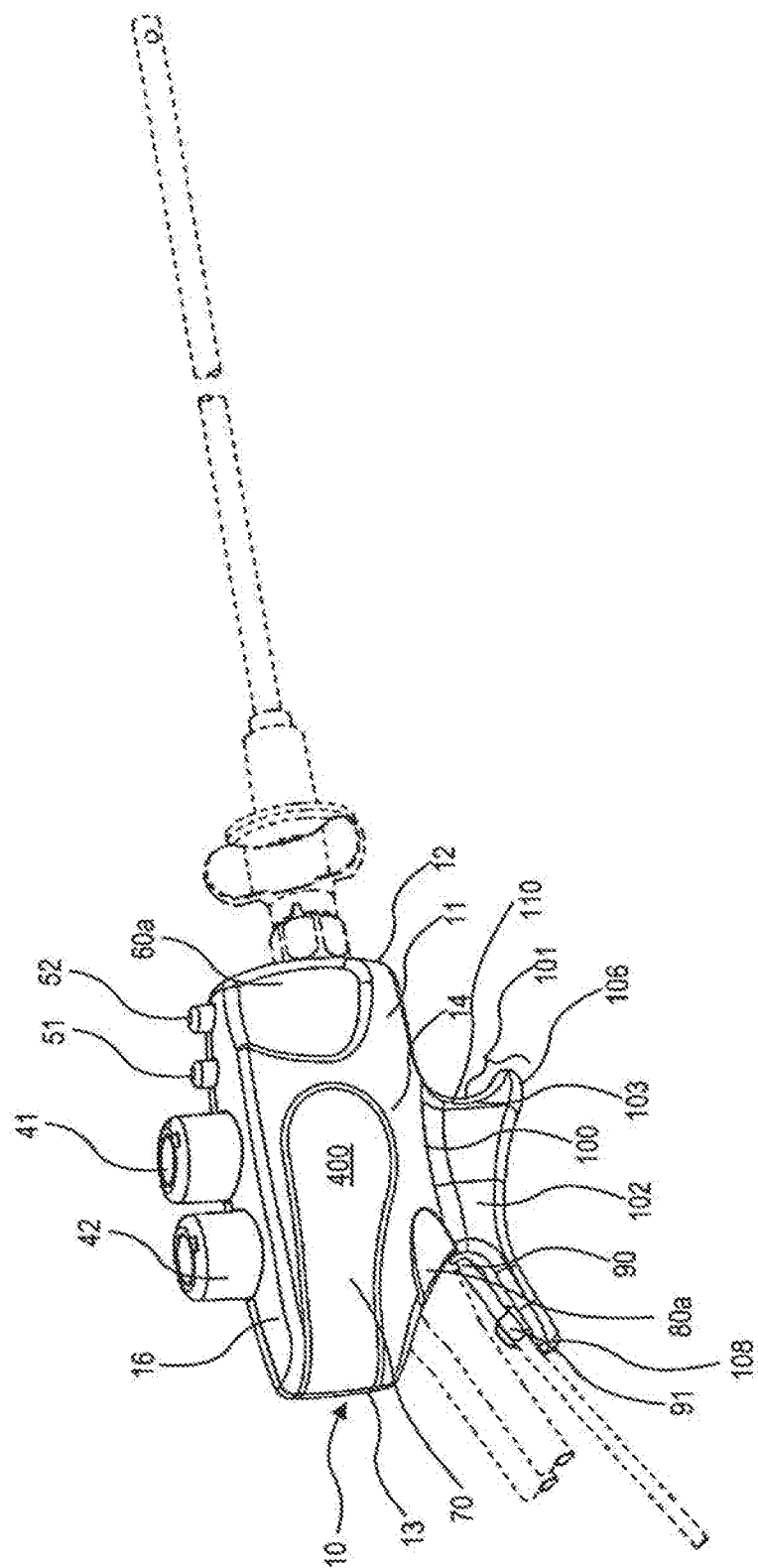
FIG. 6 is an angled side view of a medical device handpiece having an instrument connected a front end thereof, according to an embodiment of the present disclosure.

Referring to FIG. 6, there is depicted an angled side view of a medical device having an instrument connected to a front end of the handpiece. FIG. 6 is similar to the configuration of FIG. 1, with the exception that the medical instrument 20, tubing 30, and wiring 53 are all depicted in broken lines. FIG. 4, like FIG. 1, depicts an embodiment where control buttons 41, 42, 51, and 52 are all located along the same linear path along the top surface 16.

Figure 7:
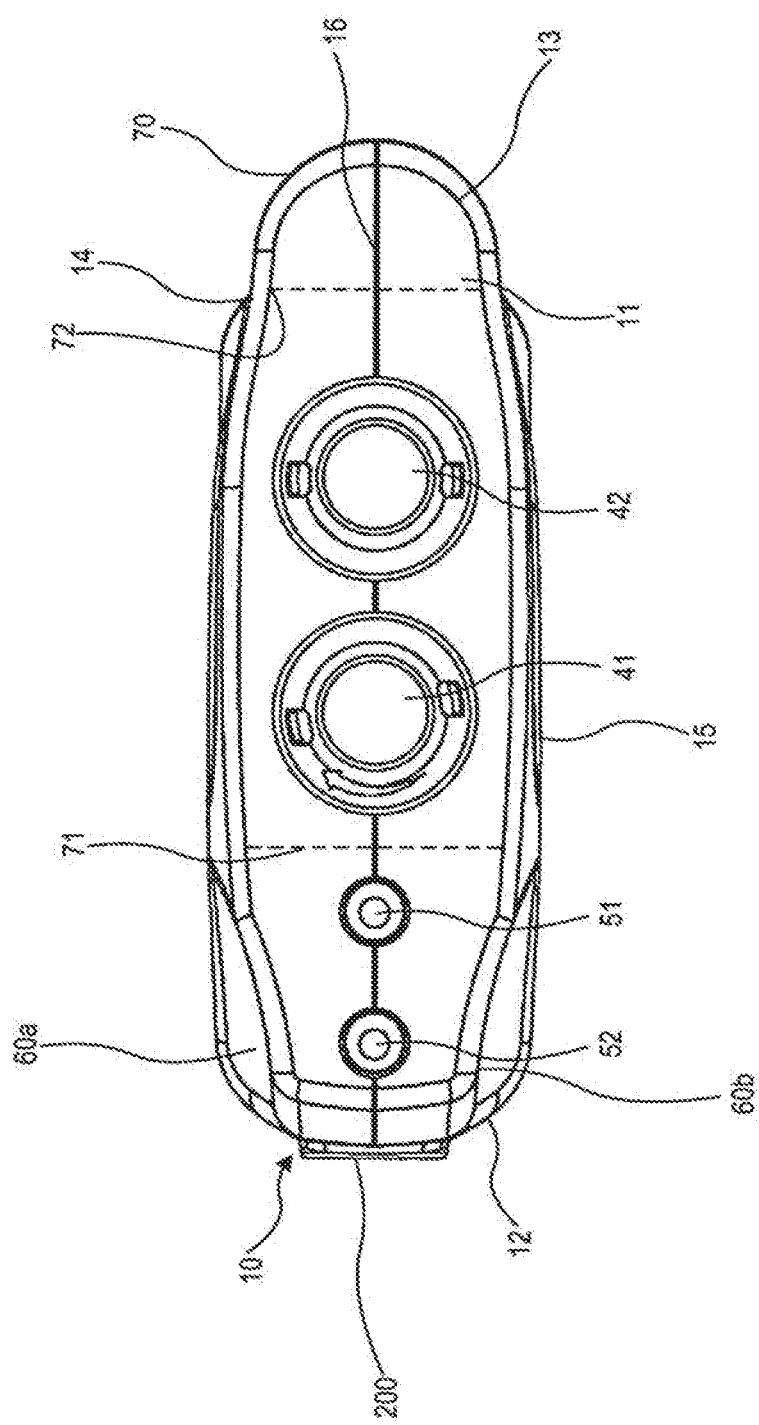
FIG. 7 is a top view of the handpiece housing of the medical device handpiece of FIG. 6, according to an embodiment of the present disclosure.

Referring to FIG. 7, there is depicted a top view of the handpiece of the medical device of FIG. 6. Just as in FIG. 4, FIG. 7 depicts lines 71 and 72, illustrating that the width of the handpiece housing 11 decreases toward a proximal end thereof.

Figure 8:
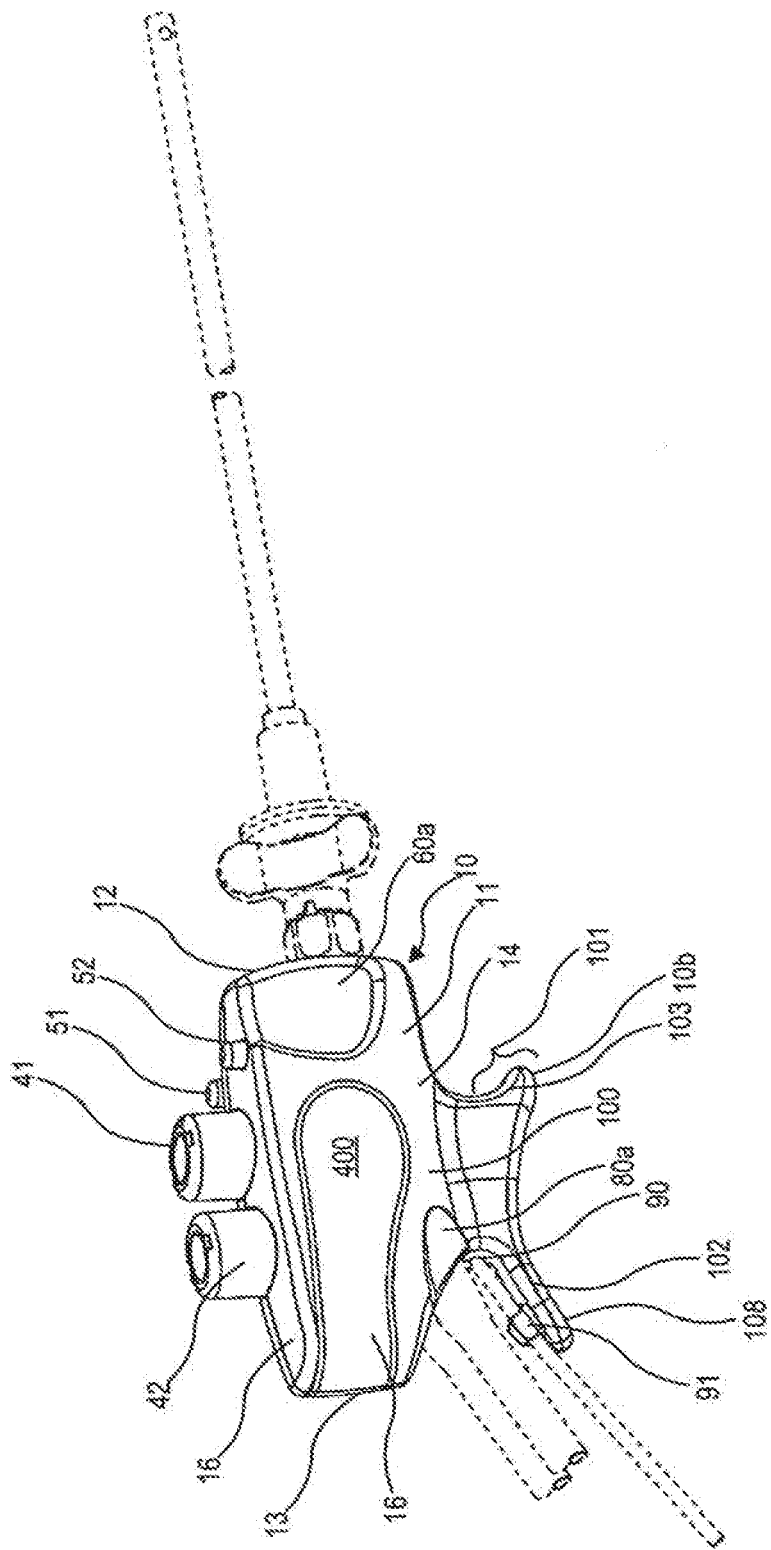
FIG. 8 is an angled side view of a medical device handpiece having an instrument connected a front end thereof, according to an embodiment of the present disclosure.

Referring to FIG. 8, there is depicted an angled side view of a medical device having an instrument connected to a front end of the handpiece. FIG. 8 is similar to the configuration of FIG. 1, with the exception that the medical instrument 20, tubing 30, and wiring 53 are all depicted in broken lines. FIG. 8, unlike FIG. 1, also depicts an embodiment where control buttons 41 and 42 are located along the same linear path along the top surface 16, while control buttons 51 and 52 are located along a linear path perpendicular to the linear path of control buttons 41 and 42.

Figure 9:
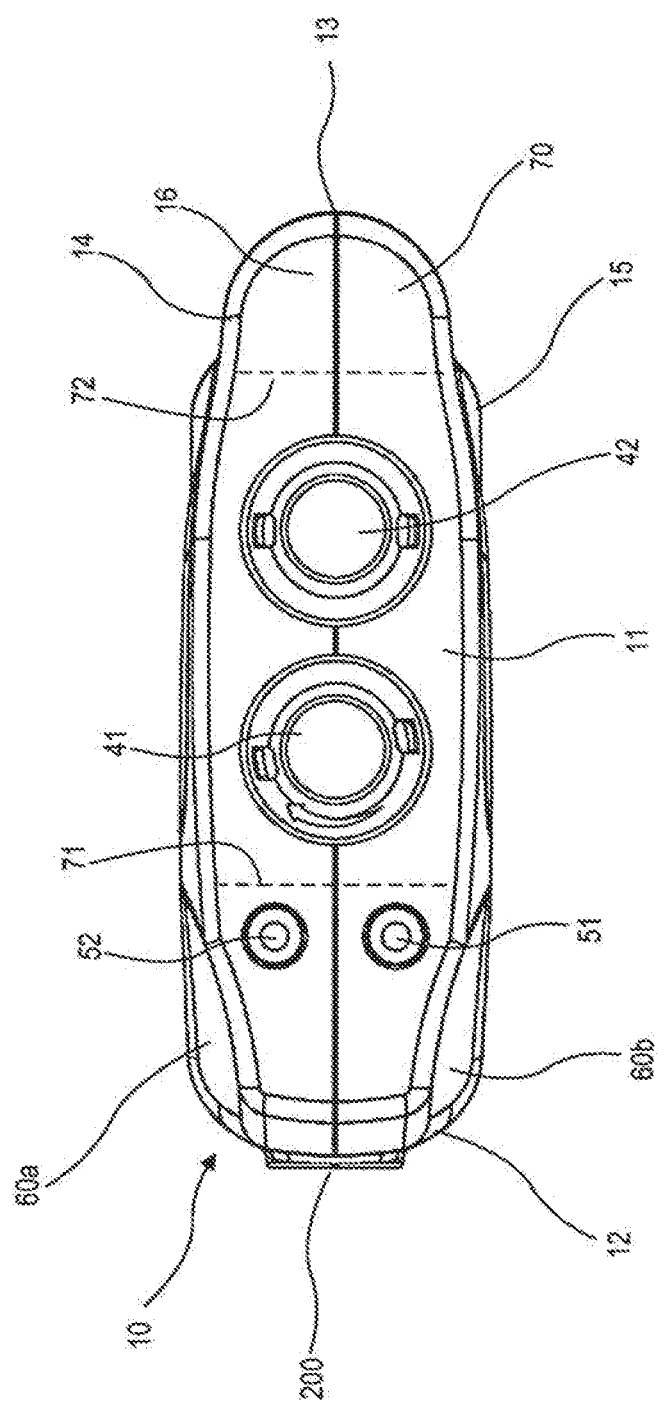
FIG. 9 is a top view of the handpiece housing of the medical device handpiece of FIG. 8, according to an embodiment of the present disclosure.

Referring to FIG. 9, there is depicted a top view of the handpiece of the medical device of FIG. 8. Just as in FIG. 4, FIG. 9 depicts lines 71 and 72 illustrating that the width of the handpiece housing 11 decreases toward a proximal end thereof. Additionally, FIG. 9 depicts the location of control buttons 51 and 52 perpendicular to the linear path of control buttons 41 and 42.

Figure 10:
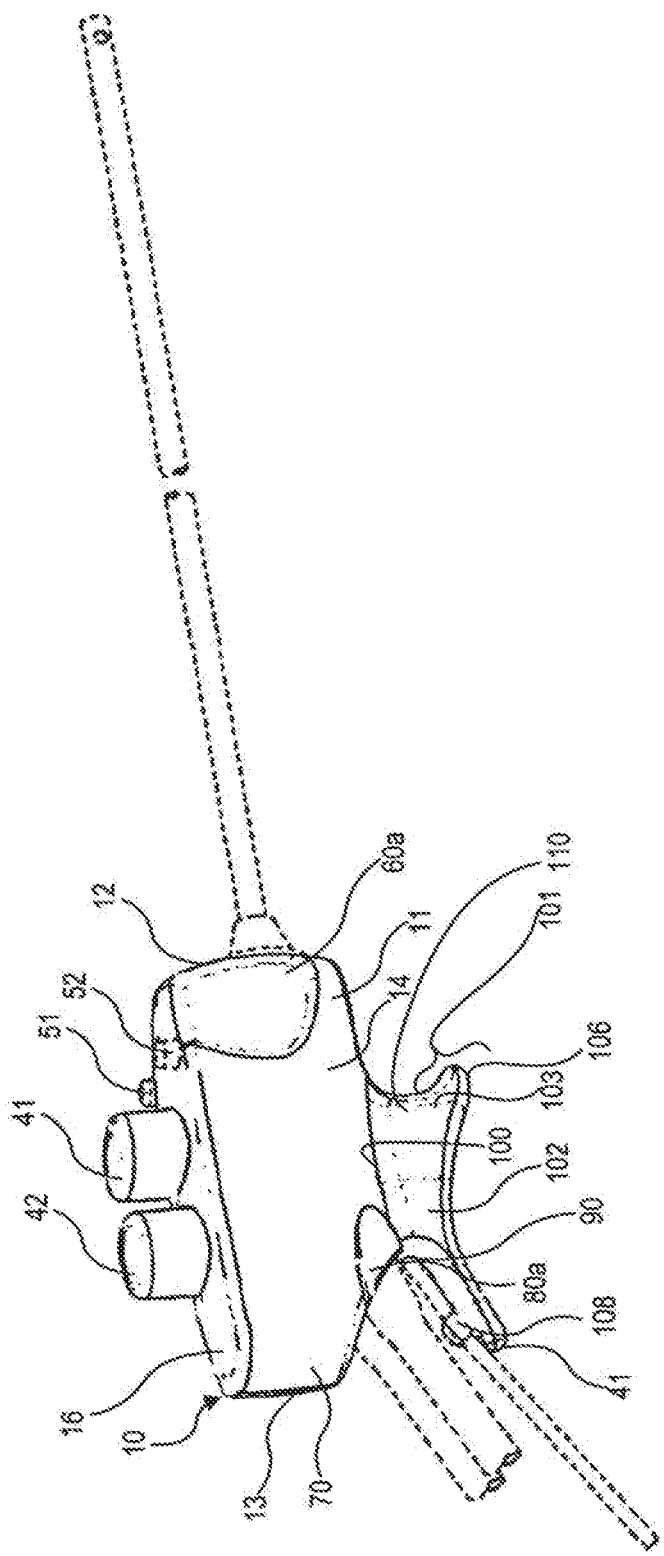
FIG. 10 is an angled side view of a medical device handpiece having an instrument connected a front end thereof, according to another embodiment of the present disclosure.

Referring to FIG. 10, there is depicted an angled side view of a medical device having an instrument connected to a front end of the handpiece. FIG. 10 is similar to the configuration of FIG. 8. FIG. 10, unlike FIG. 8, does not incorporate a gripping panel 400.

Figure 11A:
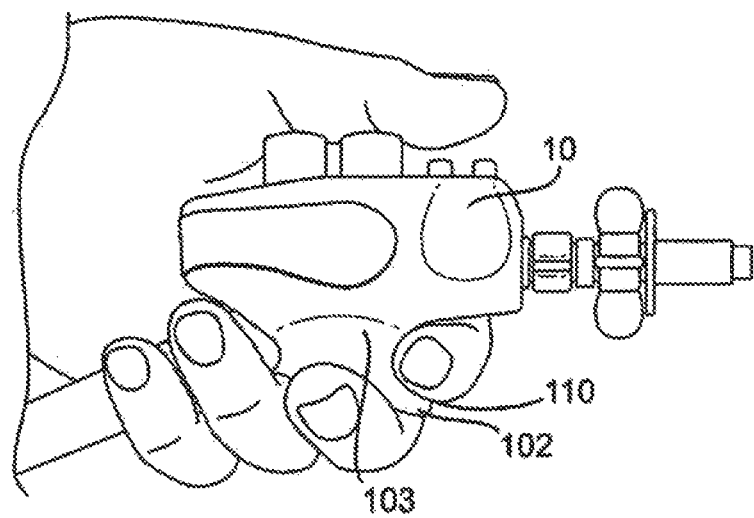
FIG. 11A illustrates an operator grasping a medical device handpiece with a left hand, according to one orientation.
Figure 11B:
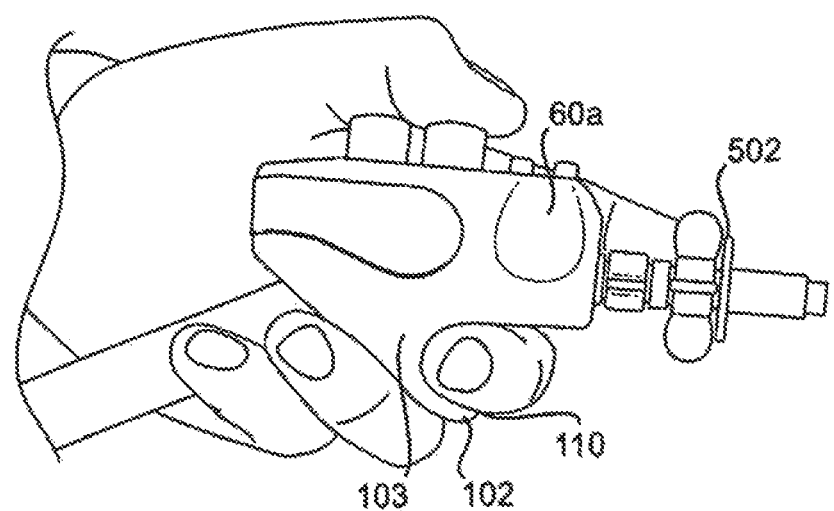
FIG. 11B illustrates an operator grasping a medical device handpiece with a left hand, according to another orientation.

FIGS. 11A-11D illustrate an operator gripping a medical device handpiece in different orientations using the left hand. In the configurations of FIGS. 11A-11B, the operator grasps the handpiece 10 such that the operator's forearm is aligned substantially parallel to the longitudinal axis longitudinal axis β (beta) of the medical instrument 20. Conversely, in FIGS. 11C-11D, the operator grasps the handpiece 10 such that the operator's forearm is aligned substantially perpendicular to the longitudinal axis β (beta) of the medical instrument 20.

For example, FIG. 11A is a side view of a medical device according to the present disclosure with the handpiece held in the left hand. As illustrated, the operator's left thumb rests over the control buttons on the top surface. At the same time, the operator's left index finger rests on the concave shaped trigger surface 110 along the neck portion 103 above the shoulder 102, while the operator's middle finger rests below the concave shaped underside surface 104 of the shoulder portion 102. In this gripping configuration, an operator can comfortably generate a grasping force with the index finger against the concave shaped surface 110 to compress the handpiece 10 comfortably between the index finger and the base of the operator's palm below the thumb.

FIG. 11B depicts a side view of a medical device in an alternative left hand gripping configuration. As illustrated in FIG. 11B, the operator's left thumb rests over the control buttons on the top surface. At the same time, the operator's left middle finger rests on the concave shaped trigger surface 110 along the neck portion 103 above the shoulder 102, while the operator's ring finger rests below the concave shaped underside surface 104 of the shoulder portion 102. In this gripping configuration, an operator's index finger is free to manipulate a base of a medical instrument such as fingertip tabs 502, as described above. Manipulation of the instrument via the index finger is further facilitated due to the clearance space provided by virtue of the inward arcuate indented portions 60a and 60b provided along the first and second halves 17, 19 of housing 11. Similar to the configuration of FIG. 11A, in FIG. 11B an operator can comfortably generate a grasping force with the middle finger against the concave shaped surface 110 to compress the handpiece 10 comfortably between the middle finger and the base of the operator's palm below the thumb.

Figure 11C:
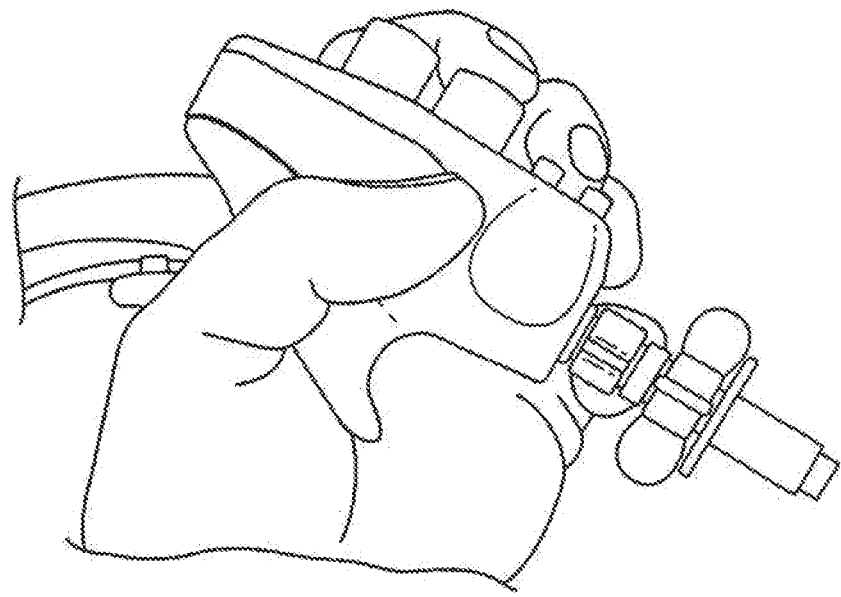
FIG. 11C illustrates an operator grasping a medical device handpiece with a left hand, according to another orientation.
Figure 11D:
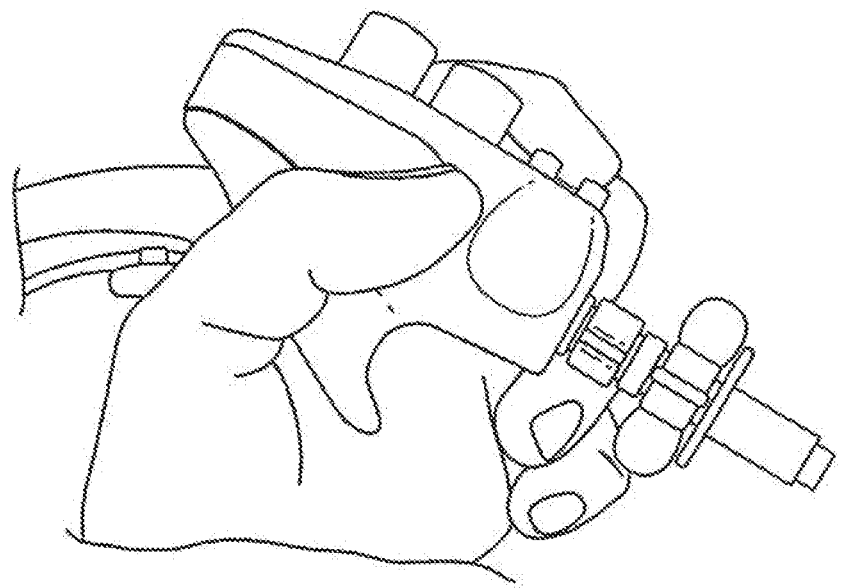
FIG. 11D illustrates an operator grasping a medical device handpiece with a left hand, according to another orientation.
Figure 12A:
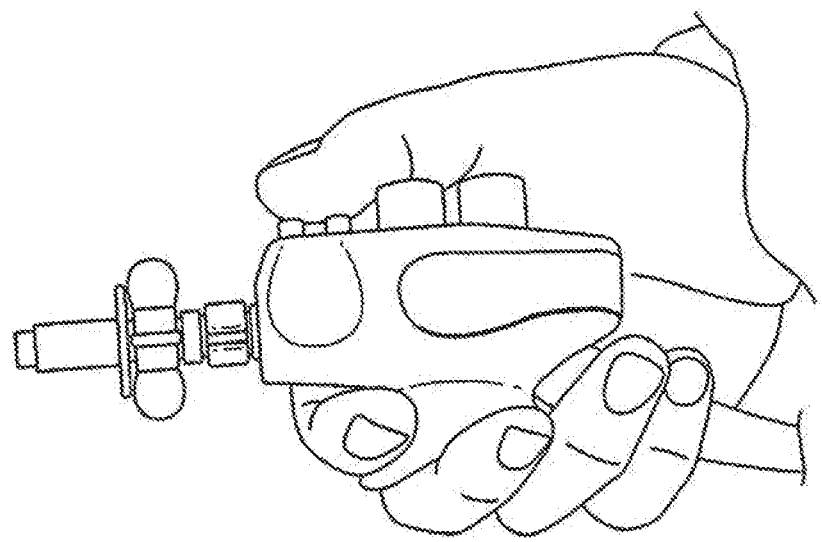
FIG. 12A illustrates an operator grasping a medical device handpiece with a right hand, according to one orientation.
Figure 12B:
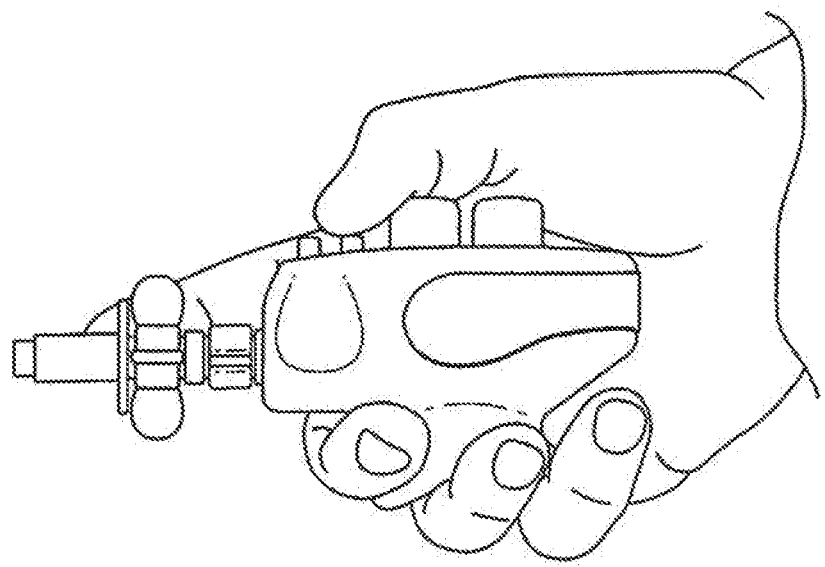
FIG. 12B illustrates an operator grasping a medical device handpiece with a right hand, according to another orientation.
Figure 12C:
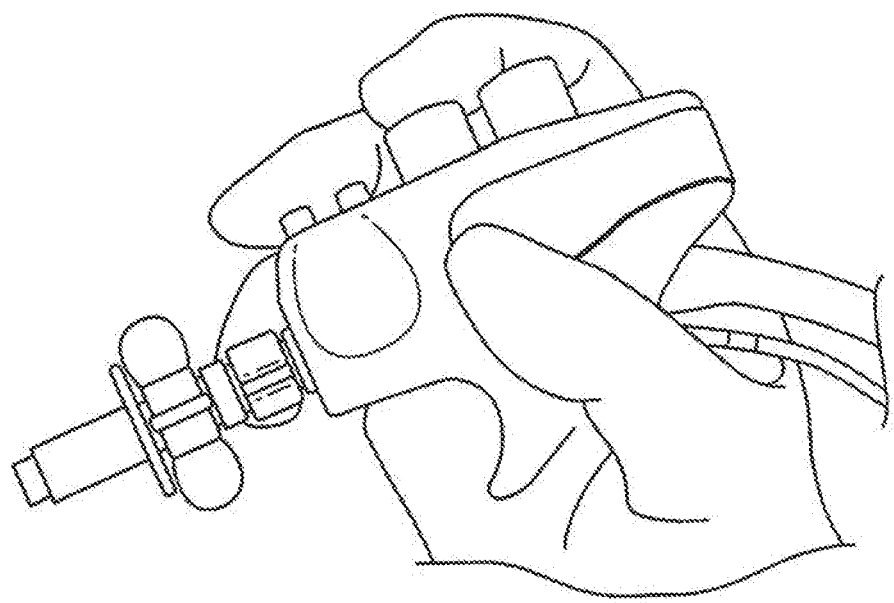
FIG. 12C illustrates an operator grasping a medical device handpiece with a right hand, according to another orientation
Figure 12D:
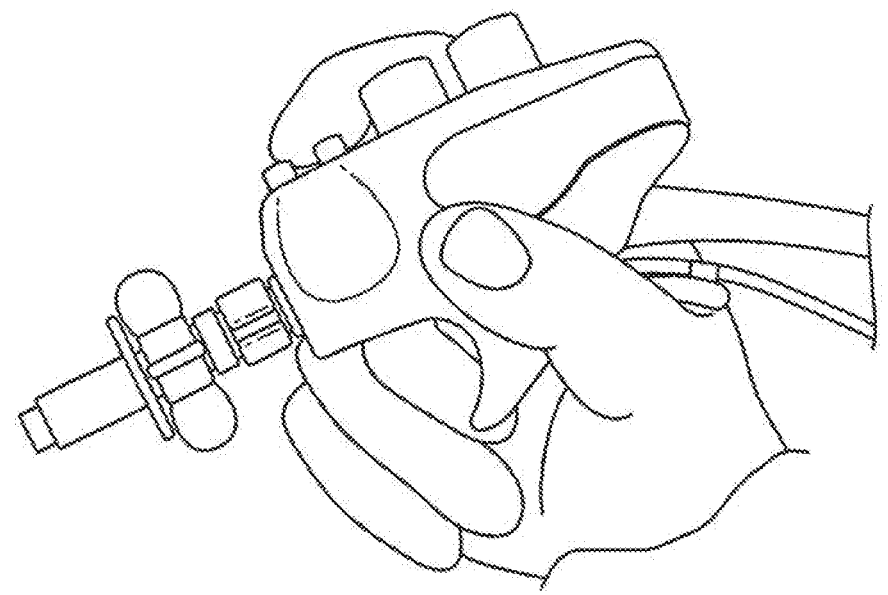
FIG. 12D illustrates an operator grasping a medical device handpiece with a right hand, according to another orientation.

FIGS. 11C and 11D depict a side view of a medical device in another alternative left hand gripping configuration. As illustrated in FIGS. 11C-11D, the handpiece 10 is grasped in the operator's left hand with the concave, curved surface 104 providing an engagement surface received within the operator's palm. More particularly, the curved surface 104 is received within the valley between the operator's thumb and index finger. In such a grasping position, an operator manipulates the control buttons with any of the fingertips while grasping opposite sides of the gripping panel 400 between the thumb and a portion of the same hand where the operator's palm meets the base of the fingers. Accordingly, in the position of FIGS. 11C-11D, the operator's grip is enhanced due to the increased friction generated by virtue of contact between (1) the operator's thumb and the portion of gripping panel 400 along the first (right) half 17 of handpiece 10 and (2) the operator's palm and the portion of gripping panel 400 along the second (left) half 19.

FIGS. 12A-12D illustrate an operator gripping a medical device handpiece in different orientations using the right hand. The gripping configurations of FIGS. 12A-12D are similar in all respects to the configurations of FIGS. 11A-11D, respectively, except the configurations of FIGS. 12A-12D depict manipulation of the handpiece 10 with an operator's right hand. As explained above, the configuration of the exterior surface of the handpiece 10 can be provided to exhibit a substantially symmetrical configuration relative to an imaginary plane that bisects the handpiece 10, through the top surface 16. As such, the handpiece 10 will conform to an operator's grip in the same manner regardless of whether an operator grasps the handle in the right hand or the left hand.

The invention has been described with reference to various and specific embodiments and techniques. It will be understood, however, that reasonable modifications and variations are possible without substantially departing from the spirit and scope of the invention. For example, additional grasping orientations, in addition to those expressly described above, are contemplated. Accordingly, the above described orientations are not intended to represent an exclusive list of potential gripping configurations.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method for operating a medical device to perform a medical procedure, comprising:
    providing a medical device comprising:
        a medical instrument connected to a front end of a handpiece, the handpiece including an attachment structure along a front end thereof configured for removably coupling to the medical instrument, the handpiece further comprising a housing, the housing comprising:
            a top surface defining at least one hole for receiving at least one button for controlling a function of the medical device;
            a bottom base; and
            an extension portion connected to the base and extending downwardly therefrom, the extension portion including a shoulder connected to the base by a narrowed neck portion located between the shoulder and the top surface of the housing, an outer circumference of the narrowed neck portion being smaller than an outer circumference of the shoulder, the shoulder having an underside surface having a generally concave shaped, curved surface;
            wherein the base, the shoulder, and the narrowed neck portion define a concave shaped surface capable of receiving an operator's finger; grasping the handpiece with one of a left hand or a right hand such that the operator's thumb rests over the control button, and an operator's finger rests on the concave shaped surface, the handpiece capable of being grasped by the left hand or the right hand in the same manner;
    positioning the medical instrument; and
    actuating the control button to perform a medical procedure.

2. The method of claim 1, wherein actuating the control button comprises one of supplying suction or irrigation to the medical instrument.

3. The method of claim 1, wherein actuating the control button comprises providing electric current to the medical instrument.

4. The method of claim 1, wherein a proximal portion of the medical instrument includes a rotatable element configured to control the angular orientation of the medical instrument, the method further comprising rotating the rotatable element with a finger of the same hand used to grasp the handpiece in order to change the angular orientation of the medical instrument relative to the handpiece.

5. The method of claim 1, wherein grasping the handpiece comprises receiving the concave shaped, curved surface of the shoulder within an operator's palm within a valley between an operator's thumb and index finger.

* * * * *